United States Patent [19]
Singh et al.

[11] Patent Number: 5,925,633
[45] Date of Patent: *Jul. 20, 1999

[54] 3-SUBSTITUTED-4-OXA-1-AZABICYCLO [3,2, 0]HEPTAN-7-ONE AS CYSTEINE PROTEASE INHIBITORS

[75] Inventors: Rajeshwar Singh; Nian E. Zhou; Deqi Guo; Jadwiga Kaleta, all of Edmonton; Ronald George Micetich, Sherwood Park, all of Canada

[73] Assignee: Synphar Laboraties, Inc., Alberta, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/611,946

[22] Filed: Mar. 6, 1996

[51] Int. Cl.$^6$ .................................................. A61K 31/395
[52] U.S. Cl. ................................................................ 514/210
[58] Field of Search ............................................. 514/210

[56] References Cited

FOREIGN PATENT DOCUMENTS

| | | |
|---|---|---|
| 603 769 | 6/1994 | European Pat. Off. . |
| WO 94/01109 | 1/1994 | WIPO . |
| WO 95/18611 | 7/1995 | WIPO . |
| WO 95/18807 | 7/1995 | WIPO . |
| WO 96/21655 | 7/1996 | WIPO . |

OTHER PUBLICATIONS

Singh et al. 1995–878936 H Caplus, 1995 (copy obtained in due course).

Patent Abstracts of Japan, Publication No. JP7242600, Sep. 19, 1995.

*Primary Examiner*—Jerome D. Goldberg
*Attorney, Agent, or Firm*—Nikaido Marlelstein Murray & Oram, LLP.

[57] ABSTRACT

The use of certain 3-substituted-4-oxa-1-azabicyclo[3,2,0] heptan-7-one derivatives of general formula I,

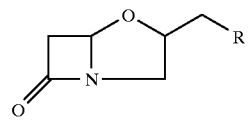

or physiologically acceptable salts thereof or isomers thereof, as active ingredients for the preparation of pharmaceutical composition and treatment of different diseases associated with deregulation of cysteine proteases is disclosed.

9 Claims, No Drawings

3-SUBSTITUTED-4-OXA-1-AZABICYCLO [3,2,0]HEPTAN-7-ONE AS CYSTEINE PROTEASE INHIBITORS

BACKGROUND OF INVENTION

Cysteine proteases, such as cathepsins B, H, L, S, and $O_2$, play a central role in a broad spectrum of medical disorders. Under normal condition, cysteine proteases function in a variety of biological processes including cell differentiation, platelet aggregation, cell invasiveness, post ribosomal processing of proteins and protein turnover. However, when cysteine proteases are deregulated in abnormal conditions, they have been implicated in a variety of diseases. Abnormal activities of lysosomal cysteine proteases have been implicated in the development and progression of a variety of human diseases, due to their ability to degrade components of extracellular matrix. Some of these diseases are cancer metastasis and invasion (Clin. Exp. Metastasis 1992, 10, 145–155; cancer metastasis rev. 1990, 9, 333–352), rheumatoid arthritis (Int. J. Biochem. 1993, 25, 545–550; Arthritis Rheumatism 1994, 37, 236–247; J Rheumatol. 1993, 20, 1176–1183; Biochem. Pharmacol. 1993, 44, 1201–1207), muscular dystrophy (Am. J. Pathol. 1986, 122, 193–198; 1987, 127, 461–466), myocardial infarction (J. Am. Coll. Cardiol. 1983, 2, 681–688), viral and parasitic infection (Rev. Infect. Dis., 1983, 5, 5914–5921) and common cold (Biochem. 1995, 34, 8172–8179).

The calcium-associated cysteine proteases calpains I and II have been associated with osteoporosis, ischemia and hypoxia, Alzheimer's disease (Proc. Natl. Acad. Sci. U.S.A. 1993, 90, 2628–2632) and cataracts (J. Biol. Chem. 1993, 268, 1937–1940).

Cathepsin B and L have been shown to have the ability to degrade type IV collagen, laminin, fibronectin, and elastin (the components of extracellular matrix), at both acidic and neutral pH. (*Annual Reports in Medicinal Chemistry*, 1993, pp. 141–160; *Protease Inhibitors as Cancer Chemopreventative Agents*, 1993, pp. 199–216; *Eur. J. Clin. Chem. Clin. Biochem.*, 30: 69–74, 1992). Their consistently increased levels in many malignant cancers makes them a perfect candidate for use in the diagnostic area or in prognosis for the progression of the cancer. Elevated levels of Cathespin L and B have been found in kidney, testicular, colon, breast, lung, bladder and ovarian cancer patients. (*Eur. J. Clin. Chem. Clin. Biochem.*, 30: 69–74, 1992; *Med. Sci. Res.*, 22: 31–32, 1994; *The Journal of Urology*, 144: 798–804, 1990; *Neoplasma*, 37.1:61–71, 1990; *Cancer Research*, 51: 1137–1142, 1991; *Cancer*, 74: 46–51, 1994). In addition, the expression of these enzymes correlates with tumor progression and shortened patient survival, in which a high level of Cathespin B was very indicative of a significantly shorter survival rate. (*American Journal of Pathology*, 145.2: 301–309, 1994; *Cancer Research*, 52: 3610–3614, 1992). It is clear that cysteine proteases are, therefore, excellent targets for the development of specific inhibitors as possible therapeutic agents.

Several types of cysteine proteases inhibitors have been reported, such as peptide aldehyde (Biochem.. Biophys. Acta 1991, 1073–43), nitrites (Biochem.. Biophys. Acta 1990, 1035, 62–70), halomethyl ketones (Anal. Biochem. 1985, 149, 461–465; Acta. Biol. Med.Ger. 1981, 40, 1503–1511; Biochem. Phar. 1992, 44, 1201–1207), (Biochem. J. 1988, 253, 751), acyloxy methyl ketones (J. Med. Chem. 1994, 37, 1833–1840; J. Am. Chem. Soc. 1988, 110, 4429–4431), ketomethylsulfonium salt (J. Biol. Chem. 1988, 263, 2768–2772), α-ketocarbonyl compounds (J. Med. Chem. 1993, 36, 3472–3480; 1994, 37, 2918–2929), vinyl sulfones (J. Med. Chem. 1995, 38, 3193–3196), and epoxysuccinyl derivatives (Agric. Biol. Chem. 1978, 42, 523–527). These inhibitors, in general, have a peptidyl affinity group and a group reactive towards the thiol of the cysteine residue in cysteine proteases. Some of them are clinically useful. However, the efficacy in vivo is not as much as expected on the basis of in vitro inhibitory activity and may be due to lower selectivity towards other proteases and poor pharmacokinetics. There exists a continuing need to develop new low molecular weight, nonpeptidyl cysteine proteases inhibitors with high selectivity, lower toxicity and better pharmacokinetics.

In continuation of work done related to β-lactam skeleton containing compounds for the use of β-lactamase inhibitor (U.S. Pat. No. 4,562,073, J.Med.Chem. 1987, 30, 1469), elastase inhibitor (U.S. Pat. No. 5,264,429,1993; U.S. Pat. No. 5,264,430,1993; U.S. Pat. No. 5,258,377,1993; U.S. Pat. No. 5,446,037,1995 and U.S. Pat. No. 5,439,904,1995), anticancer activity (WO 94/01109, PCT/GB95/00023, PCT/GB95/00024) and cysteine protease inhibitor, we have screened certain low molecular weight β-lactam class of compounds for cysteine protease inhibitory activity and the use of such compounds as cysteine protease inhibitor are reported in the present invention.

SUMMARY OF THE INVENTION

The present invention is based on the discovery that the pharmaceutical composition of certain 3-substituted-4-oxa-1-azabicyclo[3,2,0] heptan-7-one derivatives, which exhibit excellent cysteine protease inhibitory activity, can be used for treatment of different diseases associated with cystein protease deregulation such as cancer metastasis, arthritis, muscular dystrophy, myocardial infarction, bacterial infection or common colds and calcium-associated diseases associated with cystein proteases calpains I and II, such as osteoporosis, Alzheimer's disease, ischemia, hypoxia and cataracts. Types of cancer include kidney, testicular, colon, breast, lung, bladder and ovarian cancer.

In accordance with the present invention, there is provided the use of certain 3-substituted-4-oxa-1-azabicyclo[3,2,0] heptan-7-one derivatives of general formula I or physiologically acceptable salts thereof or optical isomers thereof, as active ingredients for the preparation of pharmaceutical composition and treatment of different diseases associated with deregulation of cysteine proteases,

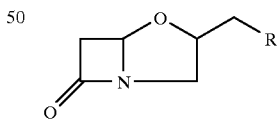

I wherein

R is selected from the group consisting of $OR_i$, —$OCOR_1$, —$COOR_1$, $CONHR_1$ $NHR_1$, —$NHCOR_1$, —$NHSO_2R_1$, $SOnR_1$ and heterocycle, wherein n is 0,1 or 2, $R_1$ is selected from the group consisting of (a) hydrogen, (b) C1–C6 alkyl which is unsubstituted or substituted by 1–3 substituents independently selected from the group consisting of $OR_2$, halogen, cyano, $NR_3R_3$, carboxy, heterocycle and phenyl, wherein the phenyl is unsubstituted or substituted by 1–2 substituents independently selected from the group consisting of $OR_2$, halogen, cyano, carboxy and $NR_3R_3$, (c) C2–C4 alkenyl which is unsubstituted or has a substituent selected from the group consisting of hydroxy, halogen, carboxy, heterocycle and phenyl, wherein the phenyl is unsubstituted or substituted by 1–2 substituents independently selected from the group consisting of $OR_2$, halogen, cyano, amino and carboxy, (d) C2–C4 alkynyl, (e) C3–C6 cycloalkyl, (f) C5–C6 cycloalkenyl, (g) a phenyl group which is unsubstituted or substituted by 1–3 substituents independently selected from the group consisting of $OR_2$, halogen, carboxy, cyano, $NR_3R_3$, C1–C4 alkyl and C1–C2 alkoxy, (h) heterocycle and (i) 1–2 amino acids in which amino groups may be protected with $R_4$ or carboxylic groups may be protected with $R_7$, heterocycle is a mono, bi or tricyclic 5–14 membered heterocyclic ring having 1–4 heteroatoms independently selected from N,S and O, $R_2$ is selected from the group consisting of (a) hydrogen, (b) C1–C4 alkyl which is unsubstituted or substituted by 1–2 substituents independently selected from the group consisting of hydroxy, halogen, cyano, carboxy, amino and phenyl and (c) a phenyl group which is unsubstituted or substituted by 1–3 substituents independently selected from the group consisting of hydroxy, halogen, carboxy, cyano, amino, C1–C4 alkyl, and C1–C2 alkoxy, $R_3$ is selected from the group consisting of (a) hydrogen, (b) C1–C4 alkyl which is unsubstituted or substituted by 1–2 substituents independently selected from group consisting of hydroxy, halogen, cyano, carboxy and amino, (c) a phenyl group which is unsubstituted or substituted by 1–3 substituents independently selected from the group consisting of hydroxy, halogen, carboxy, cyano, amino, C1–C4 alkyl, and C1–C2 alkoxy and (d) $COR_5$ wherein $R_5$ is C1–C4 alkyl or phenyl, wherein the phenyl is unsubstituted or substituted by 1–3 substituents independently selected from the group consisting of hydroxy, halogen, carboxy, cyano, amino, C1–C4 alkyl, and C1–C2 alkoxy, $R_4$ is selected from the group consisting of (a) $COOR_6$, (b) $COR_6$ and (c) $SO_2R_6$, wherein $R_6$ is selected from the group consisting of (1) C1–C4 alkyl which is unsubstituted or substituted by 1–2 substituents independently selected from (i) hydroxy, (ii) halogen, (iii) cyano, (iv) carboxy, (v) amino, (vi) phenyl, wherein the phenyl is unsubstituted or substituted by 1–3 substituents independently selected from the group consisting of hydroxy, halogen, carboxy, cyano, amino, C1–C4 alkyl and C1–C2 alkoxy and (vii) a mono or bicyclic 5–10 membered heteroaryl ring having 1–3 heteroatoms independently selected from N, S and O and (2) a phenyl group which is unsubstituted or substituted by 1–3 substituents independently selected from the group consisting of hydroxy, halogen, carboxy, cyano, amino, C1–C4 alkyl, and C1–C2 alkoxy, and $R_7$ is selected from the group consisting of (a) C1–C4 alkyl group which is unsubstituted or substituted by 1–2 substituents independently selected from the group consisting of (i) hydroxy, (ii) halogen, (iii) cyano, (iv) carboxy, (v) amino, (vi) phenyl, wherein the phenyl is unsubstituted or substituted by 1–3 substituents independently selected from the group consisting of hydroxy, halogen, carboxy, cyano, amino, C1–C4 alkyl and C1–C2 alkoxy and (vii) a mono or bicyclic 5–10 membered heteroaryl ring having 1–3 heteroatoms independently selected from N,S and O and (b) a phenyl group which is unsubstituted or substituted by 1–3 substituents independently selected from the group consisting of hydroxy, halogen, carboxy, cyano, amino, C1–C4 alkyl and C1–C2 alkoxy.

The term "1–2 amino acid" used herein is one amino acid or one dipeptide consisting of two amino acids which are bound to each other through a peptide bond.

Examples of amino acids are any of the 20 natural amino acids, i.e., α-amino acids which are the constituents of normal protein, or their optical isomers, such as glycine, D- or L-alanine, D- or L-valine, D- or L-leucine, D- or L-isoleucine, D- or L-serine, D- or L-threonine, D- or L-aspartic acid, D- or L-glutamic acid, D- or L-asparagine, D- or L-glutamine, D- or L-lysine, D- or L-arginine, D- or L-phenylalanine, D- or L-phenylglycine, D- or L-tyrosine, D- or L-methionine, D- or L-proline and the like.

Examples of heterocycles are 1,2,3-triazole, 1,2,4-triazole, imidazole, pyrrole, pyrazole, thiophene, pyrrolidine, pyridine, piperidine, pyrimidine, piperazine, morpholine, thiomorpholine, 1-quinoline, 2-quinoline, isoalloxazine, phenoxazine, phenothiazine and the like.

Examples of heteroaryl group are 1,2,3-triazole, 1,2,4-triazole, imidazole, pyrrole, pyrazole, thiophene, pyrrolidine, pyridine, pyrimidine, piperidine, piperazine, morpholine, thiomorpholine, 1-quinoline, 2-quinoline and the like.

Examples of C1–C6 alkyl group as substituents are straight or branched chain alkyl group having 1 to 6 carbon atoms such as methyl, ethyl, propyl, pentyl, hexyl, 2-methyl propyl, 3-methyl butyl, 4-methyl pentyl, 1-methyl propyl, 1-methyl butyl, 2-methylbutyl, 1-methyl pentyl and the like.

Examples of C1–C4 alkyl group as substituents are straight or branched chain alkyl group having 1 to 6 carbon atoms such as methyl, ethyl, propyl, butyl, 2-methyl propyl, 1-methyl propyl and the like.

Examples of halogen atom as substituents are fluorine, chlorine, bromine or iodine atom.

Examples of C2–C4 alkenyl group as substituents are straight chain alkenyl group having 2–4 carbon atoms such as ethenyl, 1-propenyl, 1-butenyl, 2-butenyl, 1,3 butadienyl and the like.

Examples of C2–C4 alkynyl group as substituents are ethynyl, 1-propynyl, 1-butynyl, 2-butynyl and the like.

Examples of C3–C6 cycloalkyl group as substituents are cyclopropyl, cyclobutyl, cyclopentyl, cyclohexyl and the like.

Examples of C5–C6 cycloalkenyl group as substituents are cyclopentenyl, cyclohexenyl, 2-methyl cyclopentenyl and the like.

Examples of C1–C2 alkoxy group as substituents are straight chain alkoxy group having 1–2 carbon atoms such as methoxy, ethoxy.

Examples of physiologically acceptable salts of formula I are selected from sodium, potassium, magnesium, calcium, hydrogen chloride, tartaric acid, succinic acid, fumaric acid and p-toluenesulfonic acid.

4-oxa-1-azabicyclo[3,2,0] heptan-7-one nucleus carries two asymmetric carbon atoms at position 3 and 5, and can therefore exist as 4-diastereoisomers. In general, the preferred isomer is that in which the hydrogen atoms at C3 and C5 are trans to each other which have superior inhibitory activity against different cysteine proteases such as Papain and Cathepsin B. Such diastereoisomers and their racemic mixtures are also included for use as cysteine protease inhibitors.

DESCRIPTION OF PREFERRED EMBODIMENTS

The present invention relates to the use of 3-substituted-4-oxa-1-azabicyclo[3,2,0] heptan-7-one derivatives having excellent cysteine protease inhibitory activity and selectivity among cysteine proteaess. The active ingredients of this invention are characterized by compounds having a substitution at position 3 via linkage by ester, amide, ether, thio-ether, sulphonamide and the like with 4-oxa-1-azabicyclo[3,2,0] heptan-7-one skeleton. The 3-substituted-4-oxa-1-azabicyclo[3,2,0] heptan-7-one derivatives were prepared by the general synthetic route as reported below and in J. Chem. Soc. Perkin Trans. I 2222, (1980); Tetrahedron 2467–2474 (1987); WO 94/01109, PCT/GB95/00023; PCT/GB95/00024:

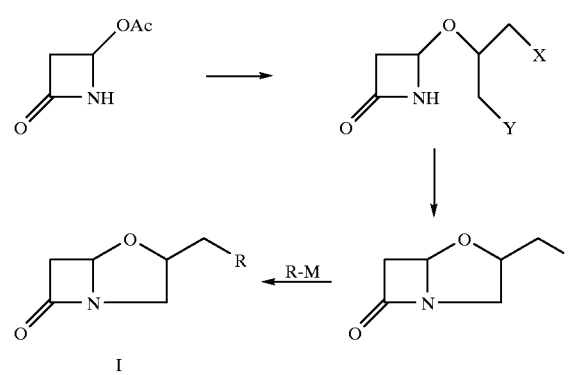

where X and Y are a good leaving group and R is a nucleophile. Suitably X and Y are a halogen atom selected from chlorine, bromine, iodine or methanesulphonyloxy. R is an OCOR$_1$ or SR$_1$. M is a sodium or potassium metal.

A further suitable transformation of compound I when R is SR$_1$, has been done by oxidation of a thio group with a suitable oxidizing agent such as m-chloroperbenzoic acid, peracetic acid or hydrogen peroxides to SOR$_1$ and SO$_2$R$_1$ as shown below (British Patent 1515241):

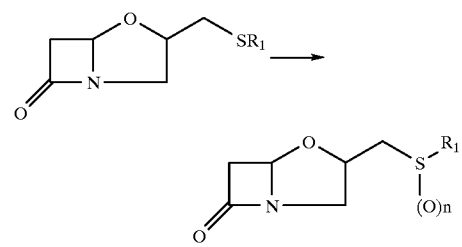

The preparation of compounds of general formula I when R is OR$_1$ was done by the known procedure as described below (Tetrahedron 2467–2474 (1987)):

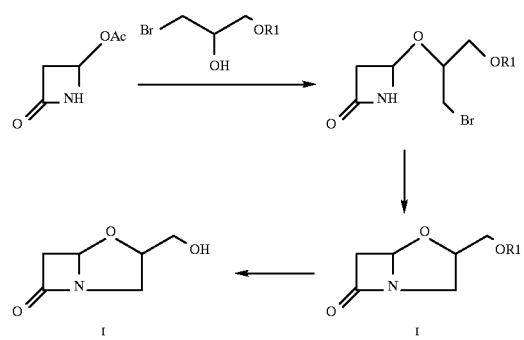

The preparation of compounds of general formula I when R is NHCOR$_1$, NHSO$_2$R$_1$ and heterocycles were done by following the synthetic scheme as shown below (PCT/GB95/00023, PCT/GB95/00024):

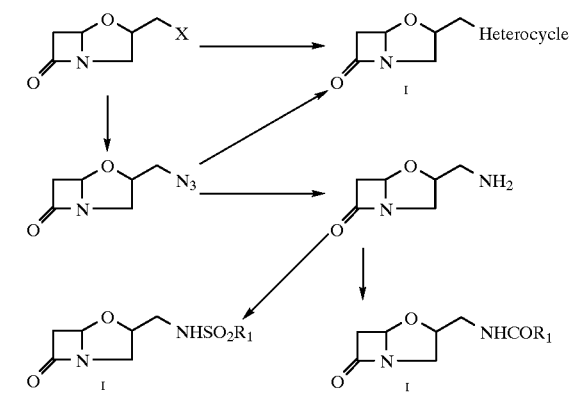

The derivatives of general formula I wherein R is NHCOR$_1$, were prepared from the amino methyl oxapenam by the reaction with acids in the presence of DCC, or with acid chloride in the presence of base, or with anhydride in the presence of base or activated ester, whereas the derivatives of general formula I wherein R is NHSO$_2$R$_1$, were prepared from the amino methyl oxapenam by the reaction with sulphony chloride in presence of base. The derivatives of general formula I wherein R is heterocycles, were prepared from 3-halo methyl oxapenam by reaction with heterocycle having free —NH or —COOH group in presence of base, or from azido methyl oxapenam with substituted or unsubstituted acetylenes (example 17).

The derivatives of general formula I wherein R is COOR$_1$ and CONHR$_1$, were prepared by following the procedure as described in experimental section (example 18–20) and synthetic scheme as follows:

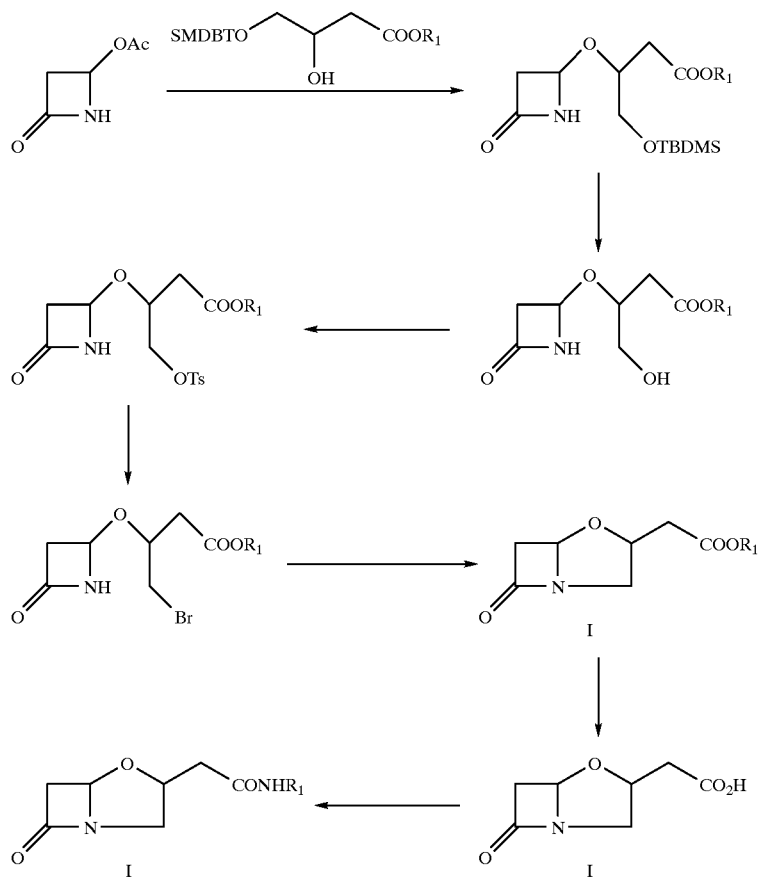

In the above processes, the reactions are reacted together with solvent at elevated or low temperatures for sufficient time to allow the reaction to proceed to completion. The reaction conditions will depend upon the nature and reactivity of the reactants. Wherever a base is used in a reaction, it is selected from the group consisting of triethyl amine, pyridine, 4-dimethylaminopyridine, diisopropylamine, 1,5-diazabicyclo [4,3,0] non-5-ene, 1,8-diazabicyclo [5,4,0] undec-7-ene, sodium carbonate, potassium carbonate and cesium carbonate. Preferred solvents for the reaction are non-reactive solvents. Depending on the reactants, a solvent will generally be selected from the group consisting of benzene, toluene, acetonitrile, tetrahydrofuran, ethanol, methanol, chloroform, ethyl acetate, methylene chloride, dimethyl formamide, dimethyl sulfoxide, hexamethyl phosphoric triamide, and the like. Solvent mixtures may also be utilized. Reaction temperatures generally range from between −70° C. to 150° C. The preferred molar ratio of reactants are 1:1 to 5. The reaction time range from 0.5 to 72 hours, depending on the reactants.

The compounds of this invention, when used as an agent for treating disease associated with cysteine protease deregulation, such as cancer metastasis, arthritis, muscular dystrophy, myocardial infarction, Alzheimer's disease, bacterial infections, common colds, osteroporosis, ischemia, hypoxia or cataracts in mammals including humans, may take pharmaceutical dosage forms including parenteral preparation such as injections, suppositories, aerosols and the like, and oral preparations such as tablets, coated tablets, powders, granules, capsules, liquids and the like. Injections are generally preferred. The above preparations are formulated in a manner known in the art.

For the formulation of solid preparations for oral administration, an excipient, and if desired, a binder, disintegrator, lubricant, coloring agent, corrigent, flavor, etc. is added to the compound of the invention, and then tablets, coated tablets, granules, powders, capsules or the like are prepared in a conventional manner.

For the formulation of injections, a pH adjusting agent, buffer, stabilizer, isotonic agent, local anesthetic or the like is added to the active ingredient of the invention. Injections for subcutaneus, intramuscular or intravenous administration can be prepared in the conventional manner.

For the formulation of suppositories, a base, and, if desired, a surfactant are added to the active ingredient of the invention, and the suppositories are prepared in a conventional manner.

The excipients useful for solid preparations for oral administration are those generally used in the art, such as lactose, sucrose, sodium chloride, starches, calcium carbonate, kaolin, crystalline cellulose, methyl cellulose, glycerin, sodium alginate, gum arabic and the like. Other ingredients which may be used in the formulations of the invention include binders such as polyvinyl alcohol, polyvinyl ether, polyvinyl pyrrolidone, ethyl cellulose, gum arabic, shellac, sucrose, water, ethanol, propanol, carboxymethyl cellulose, potassium phosphate and the like; lubricants such as magnesium stearate, talc and the like; and additives such as usual known coloring agents, disintegrators and the like. Examples of bases useful for the formulation of suppositories are oleaginous bases such as cacao butter, polyethylene glycol, lanolin, fatty acid triglycerides, Witepsol (trademark, Dynamite Nobel Co. Ltd.) and the like. Liquid preparations may be in the form of aqueous or oleaginous suspensions, solutions, syrups, elixirs and the like, which can be prepared by a conventional way using additives.

The amount of the compound of formula I of the invention to be incorporated into the pharmaceutical composition of the invention varies with the dosage form, solubility and chemical properties of the compound, administration route, administration scheme and the like. Preferable the amount is about 1 to 25 w/w % in the case of oral preparations, and about 0.1 to 5 w/w % in the case of injections which are parenteral preparations.

The dosage of the compound I of the invention is suitably determined depending on the individual cases taking symptoms, age and sex of the subject and the like into consideration. Usually the dosage in the case of oral administration is about 50 to 1500 mg per day for an adult in 2 to 4 divided doses, and the dosage in the case of injection, for example, by intravenous administration is 2 ml (about 1 to 100 mg) which is administered once a day for adults wherein the injection may be diluted with physiological saline or glucose injection liquid if so desired, and slowly administered over at least 5 minutes. The dosage in case of suppositories is about 1 to 1000 mg which is administered once or twice a day at an interval of 6 to 12 hours wherein the suppostories are administered by insertion into the rectum. Further description of the preferred embodiments can be found in the following examples, which are in no way intended to limit the scope of the present invention.

REFERENCE EXAMPLE 1

(3R, 5S)-3-(tert-butyldimethylsilyl)oxymethyl-4-oxa-1-azabicyclo [3,2,0] heptan-7-one (Ref. Ex. 1A) and (3R, 5R)-3-(tert-butyldimethylsilyl)oxymethyl-4-oxa-1-azabicyclo [3,2,0] heptan-7-one (Ref. Ex. 1B)

A mixture of 4-[(S)-1-(tert-butyldimethylsilyl)oxymethyl-2-iodoethoxy]-azetidin-2-one which was prepared by the known method (6.8 g, 17.7 mmole), and powdered $K_2CO_3$ (6.1 g, 44 mmole) in DMSO (100 ml) was stirred at room temperature overnight and then diluted with ethyl acetate, washed with water, brine, and dried over sodium sulfate. After removal of solvent, the residue was purified by repeated silica gel column chromatography using hexane-ethyl acetate (9:1) as eluent. The title compounds (3R, 5S)-3-(tert-butyldimethyl silyl)oxymethyl-4-oxa-1-azabicyclo [3,2,0] heptan-7-one (Ref. 1A) (1.85 g, yield 41%) and its isomer (3R, 5R)-3-(tert-butyldimethyl silyl) oxymethyl-4-oxa-1-azabicyclo [3,2,0] heptan-7-one (Ref. 1B) (1.28 g, yield 28%) were obtained as oil.

For Ref.1A:
$[\alpha]_D^{22}$=−95° (c=2, CHCl3);
FAB-MS: 258 (MH$^+$), calcd for $C_{12}H_{23}NO_3$ 257
IR (Nujol, cm$^{-1}$): 2930, 1770, 1460.
$^1$H NMR (CDCl$_3$), δ(ppm): 0.08 (6H, s), 0.90 (9H, s), 2.77 (1H, d, J=16), 2.92 (1H, dd, J=11, 5), 3.22 (1H, d, J=16, 3), 3.5–3.8 (2H, m), 3.89 (1H, dd, J=11, 7), 4.2–4.6 (1H, m), 5.31 (1H, d, J=3).
For Ref.1B:
$[\alpha]_D^{22}$=+93° (c=2, CHCl3):
FAB-MS: 258 (MH$^+$), calcd for $C_{12}H_{23}NO_3$ 257
IR (Nujol, cm$^{-1}$): 2935, 1790, 1459.
$^1$H NMR (CDCl$_3$), δ (ppm): 0.08 (6H, s), 0.88 (9H, s), 2.83 (1H, d, J=16.1), 3.09 (1H, dd, J=10.8, 7.0), 3.23 (1H, d, J=16.1, 2.3), 3.6–3.75 (3H, m), 4.30–4.45 (1H, m), 5.22 (1H, d, J=2.3).

REFERENCE EXAMPLE 2
(3R, 5S)-3-hydroxymethyl-4-oxa-1-azabicyclo[3,2,0] heptan-7-one (Ref. Ex. 2)

A THF solution of 1N $Bu_4NF$ (2.71 ml, 2.71 mmole) containing AcOH (90 mg, 1.5 mmole) was added to a solution of ref. compound 1A (465 mg, 1.81 mmole) in THF (5 ml) at 0–5° C. The mixture was stirred at room temperature for 2 hrs, then poured into a silica gel column. The column was eluented with hexane-ethyl acetate (1:2) and 250 mg of title compound was obtained as an oil.
Yield: 96%.
$[\alpha]_D^{22}$=−144° (c=2, CHCl3);
$^1$H NMR (CDCl$_3$), δ (ppm): 1.80–2.10 (1H, br), 2.86 (1H, d, J=16.1), 2.88 (1H, dd, J=11.1, 5.8), 3.31 (1H, dd, J=16.1, 2.6), 3.62 (1H, dd, J=12, 4.8), 3.81 (1H, dd, J=12, 3.3), 3.94 (1H, dd, J=11.6, 6.8), 4.35–4.5 (1H, m), 5.36 (1H, d, J=2.6).

REFERENCE EXAMPLE 3
(3S,5S)-3-(N-acetylamino)methyl-4-oxa-1-azabicyclo [3,2,0] heptan-7-one (Ref. Ex. 3)

Chlorobenzenesulfonyl chloride (478 mg, 2.27 mmol) was added to an ice-cooled solution of (3R,5S)-3-hydroxymethyl-4-oxa-1-azabicyclo[3,2,0]heptan-7-one (ref. compound 2) (250 mg, 1.75 mmol) and triethylamine (230 mg, 2.27 mmol) in dichloromethane (5 ml). The mixture was stirred at room temperature over night. After removal of solvent, the residue was purified by silica gel column chromatography using chloroform-ethyl acetate (5:1) as eluent and 420 mg of (3R,5S)-3-(4-chlorobenzenesulfonyl)oxymethyl-4-oxa-1-azabicyclo[3,2,0] heptan-7-one was obtained as white solid.
Yield: 76%
$[\alpha]_D^{23}$ (CHCl$_3$): −88°
m.p.: 154–155° C.
$^1$H NMR (CDCl$_3$), δ(ppm): 2.82 (1H, d, J=16.1), 2.84 (1H, dd, J=11.6, 6.1), 3.28 (1H, dd, J=16.1, 2.6), 3.98 (1H, dd, J=11.8, 7.1), 4.09 (1H, dd, J=11, 4.5), 4.20 (1H, dd, J=11, 4.5), 4.52 (1H, m), 5.27 (1H, d, J=2.6), 7.56 (2H, d, J=8.6), 7.86 (2H, d, J=8.6).

A mixture of (3R,5S)-3-(4-chlorobenzenesulfonyl)oxymethyl-4-oxa-1-azabicyclo [3,2,0] heptan-7-one (400 mg, 1.26 mmol), sodium azide (212 mg, 3.8 mmol) and DMF (5 ml) was stirred at 65° C. for 2 hrs. The resulting mixture was diluted with ethyl acetate, washed with water, brine, and dried over sodium sulfate. After removal of solvent, the residue was purified by silica gel column chromatography using hexane-ethyl acetate (2:1) as eluent and 210 mg of (3S,5S)-3-azidomethyl- 4-oxa-1-azabicyclo [3,2,0] heptan-7-one was obtained.
Yield: 99%
$^1$H NMR (CDCl$_3$), δ(ppm): 2.86 (1H, d, J=16.6), 2.84 (1H, dd, J=11.7, 6.8), 3.25–3.40 (2H, m), 3.54 (1H, dd, J=16.6, 2.7), 3.97 (1H, dd, J=11.7, 6.8), 4.49 (1H, m), 5.39 (1H, d, J=2.7).

(3S,5S)-3-azidomethyl-4-oxa-1-azabicyclo [3,2,0] heptan-7-one (710 mg, 4.23 mmole) was hydrogenated in the presence of acetic anhydride (431 mg, 4.23 mmole) in ethyl acetate (20 ml) at 50 psi for 1 hr. After removal of solvent, the residue was purified by silica gel column chromatography using ethyl acetate-acetone (5:1) as eluent and the title compound was obtained as solid.
Yield: 89%
$[\alpha]D^{23}$ (c=1.0, CHCl$_3$): −174°
m.p.: 82.5–84.5° C.
IR (Nujol, cm$^{-1}$): 3340, 1764, 1646, 1540.
$^1$H NMR (CDCl$_3$), δ (ppm): 2.02 (3H, s), 2.68 (1H, dd, J=7.0, 11.8), 2.84 (1H, d, J=16.2), 3.26–3.40 (2H, m), 3.56 (1H, ddd, J=3.6, 6.3, 14.2), 3.96 (1H, dd, J=6.4, 11.8), 4.31–4.43 (1H, m), 5.33 (1H, d, J=2.5), 5.86 (1H, br, s).

EXAMPLE 4
(3RS,5SR)-3-{N-(benzyloxycarbonyl)-L-phenylalanyl}-oxymethyl-4-oxa-1-azabicyclo [3,2,0] heptan-7-one (Ex. 4)

A mixture of N-(benzyloxycarbonyl)-L-phenylalanine (150 mg, 0.5 mmol), cesium carbonate (180 mg, 0.55 mmol) and hexamethyl phosphoric triamide (2 ml) was stirred at room temperature for 1 hr, and then (3RS, 5SR)-3-bromomethyl- 4-oxa-1-azabicyclo [3,2,0] heptan-7-one (100 mg, 0.49 mmol) in hexamethyl phosphoric triamide (2 ml) was added. The above mixture was stirred at 55° C. for 4 hrs and then diluted with ethyl acetate, washed with water, brine, and dried over sodium sulfate. After removal of solvent, the residue was purified by silica gel column chromatography using hexane-ethyl acetate (2:1) as eluent and 80 mg of the title compound was obtained.
Yield: 38%
m.p.: 79.5–81° C.
FAB-MS: 425 (MH$^+$), calcd for $C_{23}H_{24}N_2O_6$ 424
IR (KBr, cm$^{-1}$): 3325, 2930, 1776, 1734, 1711, 1643, 1513.
$^1$H NMR (CDCl$_3$), δ (ppm): 2.55–2.75 (1H, m), 2.82 (1H, d, J=16.2), 3.10 (2H, d, J=6), 3.25 (1H, dd, J=16.2, 2.5), 3.88 (1H, m), 4.0–4.2 (2H, m), 4.46 (1H, m), 4.68 (1H, m), 5.10 (2H, s), 5.23 (1H, m), 7.1–7.4 (11H, m).

EXAMPLE 5
(3RS,5SR)-3-{N-(benzyloxycarbonyl)-L-prolyl}-oxymethyl-4-oxa-1-azabicyclo[3,2,0] heptan-7-one (Ex. 5)

By a method similar to the method described in example 4, the title compound was obtained by reacting N-(benzyloxycarbonyl)-L-proline with (3RS, 5SR)-3-bromomethyl-4-oxa-1-azabicyclo [3,2,0] heptan-7-one.
Yield: 44%
FAB-MS: 375 (MH$^+$), calcd for $C_{19}H_{22}N_2O_6$ 374
IR (CHCl$_3$, cm$^{-1}$) 3005, 1773, 1740, 1693, 1648, 1413, 1347.
$^1$H NMR (CDCl$_3$), δ(ppm): 1.85–2.10 (3H, m) , 2.20–2.35 (1H, m), 2.55–2.90 (2H, m), 3.24 (1H, m), 3.45–3.65 (2H, m), 3.80–4.60 (5H, m), 5.15–5.30 (3H, m), 7.35 (5H, m).

EXAMPLE 6
(3RS,5SR) -3-{N-(benzyloxycarbonyl)-L-isoleucyl}-oxymethyl-4-oxa-1-azabicyclo [3,2,0] heptan-7-one (Ex. 6)

By a method similar to the method described in example 4, the title compound was obtained by reacting N-(benzyloxycarbonyl)-L-isoleucine with (3RS, 5SR)-3-bromomethyl-4-oxa-1-azabicyclo [3,2,0] heptan-7-one.
Yield: 85%
FAB-MS: 391 (MH$^+$), calcd for $C_{20}H_{26}N_2O_6$ 390
IR (KBr, cm$^{-1}$): 3350, 1795, 1718, 1522, 1395.
$^1$H NMR (CDCl$_3$), δ(ppm): 0.95 (6H, m), 1.20 (1H, m), 1.40 (1H, m), 1.90 (1H, m), 2.85 (1H, d, J=16), 2.80 (1H, m), 3.27 (1H, m), 3.98 (1H, dd, J=11.5, 7), 4.20–4.60 (4H, m), 5.10 (2H, s), 5.25 (1H, br), 5.33 (1H, m), 7.35 (5H, m).

EXAMPLE 7
(3RS,5SR)-3-{N-(benzyloxycarbonyl)-L-phenylalanyl-glycyl}-oxymethyl-4-oxa-1-azabicyclo [3,2,0] heptan-7-one (Ex. 7)

By a method similar to the method described in example 4, the title compound was obtained by reacting N-(benzyloxycarbonyl)-L-phenylalanyl-glycine with (3RS, 5SR) -3-bromomethyl-4-oxa-1-azabicyclo [3,2,0] heptan-7-one.
Yield: 82%
m.p.: 83–85° C.
FAB-MS: 482 (MH$^+$), calcd for $C_{25}H_{27}N_3O_7$ 481
IR (KBr, cm$^{-1}$): 3285, 2935, 1775, 1746, 1714, 1682, 1646, 1525, 1440.
$^1$H NMR (CDCl$_3$), δ(ppm): 2.75 (1H, dd, J=11.7, 6.2), 2.85 (1H, d, J=16.2), 3.10 (2H, d, J=6), 3.30 (1H, dd, J=16.2, 2.5), 3.90–4.30 (5H, m), 4.4–4.6 (2H, m), 5.08 (2H, s), 5.28 (1H, br), 5.32 (1H, d, J=2.5), 6.40 (1H, br), 7.15–7.40 (10H, m).

EXAMPLE 8
(3RS, 5SR)-3-{N-(benzyloxycarbonyl)-L-isoleucyl-L-prolyl}-oxymethyl-4-oxa-1-azabicyclo [3,2,0] heptan-7-one (Ex. 8)

By a method similar to the method described in example 4, the title compound was obtained by reacting N-(benzyloxycarbonyl)-L-isoleucyl-L-proline with (3RS, 5SR)-3-bromomethyl-4-oxa-1-azabicyclo [3,2,0] heptan-7-one.
Yield: 89%
FAB-MS: 488 (MH$^+$), calcd for $C_{25}H_{33}N_3O_7$ 487
IR (KBr, cm$^{-1}$): 3325, 2945, 1778, 1735, 1692, 1526, 1444, 1408, 1345.
$^1$H NMR (CDCl$_3$), δ (ppm): 0.88 (6H, m), 1.10 (1H, m) 1.35 (1H, m), 1.90 (4H, m), 2.40 (1H, m), 2.80 (1H, m), 2.85 (1H, d, J=16), 3.28 (1H, dd, J=16, 2.5), 3.52 (2H, m), 3.97 (1H, dd, J=11.5, 7), 41.5–4.55 (5H, m), 5.15 (2H, m), 5.33 (1H, m), 7.35 (6H, m).

EXAMPLE 9
(3RS, 5SR)-3-{N-(benzyloxycarbonyl)-L-leucyl-L-prolyl}-oxymethyl-4-oxa-1-azabicyclo [3,2,0] heptan-7-one (Ex. 9)

By a method similar to the method described in example 4, the title compound was obtained by reacting N-(benzyloxycarbonyl)-L-leucyl-L-proline with (3RS, 5SR)-3-bromomethyl-4-oxa-1-azabicyclo [3,2,0] heptan-7-one.
Yield: 92%
m.p.: 97–98° C.
FAB-MS: 488 (MH$^+$), calcd for $C_{25}H_{33}N_3O_7$ 487
IR (KBr, cm$^{-1}$): 3290, 2945, 1776, 1747, 1666, 1537, 1461, 1419, 1348.
$^1$H NMR (CDCl$_3$), δ (ppm): 0.90 (6H, m), 1.60 (2H, m), 1.90 (4H, m), 2.40 (1H, m), 2.82 (1H, m), 2.85 (1H, d, J=16), 3.30 (1H, dd, J=16, 2.5), 3.52 (2H, m), 3.97 (1H, dd, J=11.5, 7), 41.5–4.55 (5H, m), 5.15 (2H, m), 5.35 (1H, m), 7.25 (1H, br), 7.35 (5H, m).

EXAMPLE 10
(3RS, 5SR)-3-(1,2-dihydro-4-methyl-2-oxo-guinolin-3-yl)-carbonyloxymethyl-4-oxa-1-azabicyclo [3,2,0] heptan-7-one (Ex. 10)

By a method similar to the method described in example 4, the title compound was obtained by reacting 1,2-dihydro-4-methyl-2-oxo-3-quinolinecarboxylic acid with (3RS, 5SR)-3-bromomethyl-4-oxa-1-azabicyclo [3,2,0] heptan-7-one.
Yield: 40%
m.p.: 210° C. (dec.)
FAB-MS: 329 (MH$^+$), calcd for $C_{17}H_{16}N_2O_5$ 328
IR (KBr, cm$^{-1}$): 2940, 1774, 1726, 1643, 1554, 1493, 1424.
$^1$H NMR (CDCl$_3$), δ (ppm): 2.54 (3H, s), 2.84 (1H, d, J=16.2), 3.10 (1H, dd, J=11.7, 6.2), 3.24 (1H, dd, J=16.2, 2.5), 4.08 (1H, dd, J=11.6, 6.9), 4.56 (2H, m), 4.17 (1H, m), 5.43 (1H, d, J=2.5), 7.26–7.40 (2H, m), 7.58 (1H, m), 7.75 (1H, d, J=7.5), 12.60 (1H, s).

EXAMPLE 11
(3RS,5SR)-3-(cyclohexanecarbonyloxymethyl)-4-oxa-1-azabicyclo [3,2,0] heptan-7-one (Ex. 11)

By a method similar to the method described in example 4, the title compound was obtained by reacting cyclohexanecarboxylic acid with (3RS, 5SR)-3-bromomethyl-4-oxa-1-azabicyclo [3,2,0] heptan-7-one.
Yield: 75%
FAB-MS: 254 (MH$^+$), calcd for $C_{13}H_{19}NO_4$ 253
IR (CHCl$_3$, cm$^{-1}$): 3010, 2850, 1774, 1722, 1646, 1441.
$^1$H NMR (CDCl$_3$), δ (ppm): 1.20–2.00 (10H, m), 2.35 (1H, m), 2.81 (1H, m), 2.85 (1H, d, J=16.1), 3.30 (1H, dd, J=16.1, 2.5), 3.97 (1H, dd, J=11.6, 7.1), 4.17 (2H, m), 4.56 (1H, m), 5.35 (1H, d, J=2.5).

EXAMPLE 12
(3RS,5SR)-3-(cyclopentanecarbonyloxymethyl)-4-oxa-1-azabicyclo [3,2,0] heptan-7-one (Ex. 12)

By a method similar to the method described in example 4, the title compound was obtained by reacting cyclopentanecarboxylic acid with (3RS, 5SR)-3-bromomethyl-4-oxa-1-azabicyclo [3,2,0] heptan-7-one.

Yield: 55%
FAB-MS: 240 (MH$^+$), calcd for $C_{12}H_{17}NO_4$ 239
IR (CHCl$_3$, cm$^{-1}$): 3000, 2865, 1774, 1721, 1646, 1440, 1353.
$^1$H NMR (CDCl$_3$), δ (ppm): 1.50–2.00 (8H, m), 2.70–2.85 (2H, m), 2.86 (1H, d, J=16), 3.30 (1H, dd, J=16, 2.5), 3.98 (1H, dd, J=12, 7), 4.18 (2H, m), 4.57 (1H, m), 5.35 (1H, d, J=2.5).

EXAMPLE 13
(3RS, 5SR)-3-(trans-3-phenylpropenoyl)oxymethyl-4-oxa-1-azabicyclo [3,2,0] heptan-7-one (Ex. 13)

By a method similar to the method described in example 4, the title compound was obtained by reacting trans-cinnamic acid with (3RS, 5SR)-3-bromomethyl-4-oxa-1-azabicyclo [3,2,0] heptan-7-one.

Yield: 61%
m.p.: 71.5–72° C.
FAB-MS: 274 (MH$^+$), calcd for $C_{15}H_{15}NO_4$ 273
IR (KBr, cm$^{-1}$): 2950, 1780, 1697, 1623, 1311.
$^1$H NMR (CDCl$_3$), δ (ppm): 2.88 (1H, d, J=16.6), 2.85 (1H, m), 3.31 (1H, dd, J=16.6, 2.6), 3.98 (1H, dd, J=12, 7), 4.31 (2H, m), 4.62 (1H, m), 5.39 (1H, d, J=2.6), 6.47 (1H, d, J=16), 7.38–7.43 (3H, m), 7.50–7.56 (2H, m), 7.73 (1H, d, J=16).

EXAMPLE 14
(3RS, 5SR)-3-(10-methylisoalloxazin-7-yl)-carbonyloxymethyl-4-oxa-1-azabicyclo [3,2,0] heptan-7-one (Ex. 14)

By a method similar to the method described in example 4, the title compound was obtained by reacting 10-methylisoalloxazine-7-carboxylic acid with (3RS, 5SR)-3-bromomethyl-4-oxa-1-azabicyclo [3,2,0] heptan-7-one.

Yield: 7%
m.p.: 250° C. (dec.)
FAB-MS: 398 (MH$^+$), calcd for $C_{28}H_{15}N_5O_6$ 397
$^1$H NMR (DMSO-d$_6$), δ(ppm): 2.81–3.02 (2H, m), 3.30 (1H, dd, J=16.1, 2.5), 3.97 (4H, m), 4.45 (2H, d, J=4.9), 4.75 (1H, m), 5.40 (1H, d, J=2.5), 8.04 (1H, d, J=9.0), 8.38 (1H, dd, J=8.9, 1.9), 8.56 (1H, d, J=1.9), 11.5 (1H, s)

EXAMPLE 15
(3RS, 5SR)-3-(7-ethoxycarbonyl-10-methylisoalloxazin-3-yl) -methyl-4-oxa-1-azabicyclo [3,2,0] heptan-7-one (Ex. 15)

By a method similar to the method described in example 4, the title compound was obtained by reacting 7-ethyloxycarbonyl-10-methylisoalloxazine with (3RS, 5SR)-3-bromomethyl-4-oxa-1-azabicyclo [3,2,0] heptan-7-one.

Yield: 9%
FAB-MS: 426 (MH$^+$), calcd for $C20H_{19}N_5O_6$ 425
$^1$H NMR (CDCl$_3$), δ (ppm): 1.45 (3H, t, J=7.2), 2.76 (1H, d, J=16.1), 2.90 (1H, dd, J=4.0, 11.3), 3.26 (1H, dd, J=2.6, 16.1), 3.94–4.05 (2H, m), 4.16 (3H, s), 4.41–4.61 (3H, m), 4.90 (1H, m), 5.51 (1H, d, J=2.5), 7.7 (1H, d, J=9.0), 8.56 (1H, dd, J=1.9, 9.0), 9.01 (1H, d, J=1.9).

EXAMPLE 16
(3RS, 5SR)-3-(1,2-dihydro-4-methyl-2-oxo-quinolin-3-yl)-carbonylaminomethyl-4-oxa-1-azabicyclo [3,2,0] heptan-7-one (Ex. 16)

(3RS, 5SR)-3-azidomethyl-4-oxa-1-azabicyclo [3,2,0] heptan-7-one (150 mg, 0.89 mmol) was hydrogenated with 100 mg of 10% palladium on activated carbon in 25 ml of ethyl acetate at 50 psi hydrogen pressure at room temperature for 1 hr. After removal of catalyst by filtration, (3RS, 5SR)-3-aminomethyl-4-oxa-1-azabicyclo [3,2,0] heptan-7-one in ethyl acetate was obtained.

A mixture of 1,2-dihydro-4-methyl-2-oxo-3-quinolinecarboxylic acid (203 mg, 1 mmol) and thionyl chloride (4 ml) was refluxed for 30 min. After removal of thionyl chloride under vacuum, a precooled (ca. −15° C.) solution of (3RS, 5SR) -3-aminomethyl-4-oxa-1-azabicyclo [3,2,0] heptan-7-one in ethyl acetate, which obtained from hydrogenation of (3RS, 5SR)-3-azidomethyl-4-oxa-1-azabicyclo [3,2,0] heptan-7-one (see above), was added at −15° C. and stirred at a bath temperature of −15 to room temperature for 3 hrs. The resulting mixture was diluted with ethyl acetate, washed with water, brine, and dried over sodium sulfate. After removal of solvent, the residue was purified by silica gel column chromatography using methanol-ethyl acetate (1:10) as eluent and 30 mg of the title compound was obtained.

Yield: 10%
m.p.: 255° C. (dec.)
FAB-MS: 328 (MH$^+$), calcd for $C_{17}H_{17}N_3O_4$ 327
$^1$H NMR (CDCl$_3$), δ (ppm): 2.67 (3H, s), 2.77 (1H, d, J=16.2), 2.95 (1H, dd, J=11.8, 7.0), 3.20 (1H, dd, J=16.2, 2.6), 3.68 (2H, m), 4.03 (1H, dd, J=11.8, 6.5), 4.51 (1H, m), 5.36 (1H, d, J=2.6), 7.21–7.28 (2H, m), 7.44 (1H, m), 7.72 (1H, d, J=7.7), 8.12 (1H, t, J=5.8), 12.60 (1H, s).

EXAMPLE 17
(3R,5S)-3-(1,2,3-triazol-1-yl)-methyl-4-oxa-1-azabicyclo [3,2,0] heptan-7-one (Ex. 17)

Acetylene (200 mg) was bubbled into a 75 ml stainless steel reaction vessel containing (3R,5S)-3-azidomethyl-4-oxa-1-azabicyclo [3,2,0] heptan-7-one (100 mg, 0.6 mmol) and acetone (20 ml) at −78° C. The reaction vessel was sealed and heated to 70° C. overnight, cooled with ice and loosen the stopcock. After removal of solvent, the residue was purified by silica gel column chromatography using chloroform-methanol (20:1) as eluent and 80 mg of (3R, 5S)-3-(1,2,3-triazol-1-yl)-methyl-4-oxa-1-azabicyclo [3,2,0] heptan-7-one was obtained.

Yield: 70%
$[α]_D^{23}$ (CHCl$_3$): −140°
m.p.: 123.5–124.2° C.
FAB-MS: 195 (MH$^+$), calcd for $C_8H_{10}N_4O_2$ 194.
IR (KBr, cm$^{-1}$): 3115, 2975, 1763, 1455, 1327.
$^1$H NMR (CDCl$_3$), δ (ppm): 2.86 (1H, d, J=16), 2.77 (1H, dd, J=12.4, 6.8), 3.31 (1H, dd, J=16, 2.8), 4.08 (1H, dd, J=12, 6.1), 4.5–4.7 (3H, m), 5.21 (1H, d, J=2.8), 7.72 (2H, d, J=7.8).

EXAMPLE 18
diphenylmethyl 2-(7-oxo-4-oxa-1-azabicyclo [3,2,0] heptan-3-yl)-acetate (Ex. 18)

A mixture of diphenylmethyl 3-hydroxy-4-(4-toluenesulfonyl)oxy-butyrate (16 g, 36 mmol), 4-acetoxyazetidin-2-one (9 g, 70 mmol), palladium acetate (1 g), triethyl amine (7.27 g, 72 mmol) and benzene (400 ml) was stirred at room temperature over night. After reaction, the precipitate was filterred off by using celite. The filtrate was washed with water, brine, and dried over sodium sulfate. After removal of solvent, the residue was purified by silica gel column chromatography using hexane-ethyl acetate (1:1) as eluent and 15 g of diphenylmethyl 3-(2-oxoazetidin-4-yl)-oxy-4-(4-toluenesulfonyl)oxy-butyrate was obtained.

Yield: 81%

$^1$H NMR (CDCl$_3$), δ (ppm): 2.45 (3H, s), 2.55–3.05 (4H, m), 3.95–4.25 (3H, m), 5.00 (1H, m), 5.97 (0.4H, br), 6.40 (0.6H, br), 6.84 (0.4H, s), 6.88 (0.6H, s), 7.32 (12H, m), 7.77 (2H, d, J=8).

A mixture of of diphenylmethyl 3-(2-oxoazetidin-4-yl)-oxy-4-(4-toluenesulfonyl) oxy-butyrate (509 mg, 1 mmol), lithium bromide (174 mg, 2 mmol) and hexamethyl phosphoric triamide (5 ml) was stirred at 65° C. under nitrogen for 2 hrs. The reaction mixture was diluted with ethyl acetate, washed with water, brine, and dried over sodium sulfate. After removal of solvent, 400 mg of diphenylmethyl 3-(2-oxoazetidin-4-yl)-oxy-4-bromo-butyrate was obtained.

Yield: 95%

$^1$H NMR (CDCl$_3$), δ (ppm): 2.75–3.10 (4H, m), 3.35–3.45 (2H, m), 4.16 (1H, m), 5.00–5.10 (1H, m), 6.35 (0.4H, br), 6.99 (0.6H, br), 6.87 (0.4H, s), 6.89(0.6H, s), 7.33 (10H, m).

A mixture of diphenylmethyl 3-(2-oxoazetidin-4-yl)-oxy-4-bromo-butyrate (9 g, 21.5 mmol), cesium carbonate (7.0 g 21.5 mmol) and dimethyl sulphoxide (100 ml) was stirred at room temperature for 4 hrs and then diluted with ethyl acetate, washed with water, brine, and dried over sodium sulfate. After removal of solvent, the residue was purified by silica gel column chromatography using hexane-ethyl acetate (2:1) as eluent and 3.2 g of diphenylmethyl 2-(7-oxo-4-oxa-1-azabicyclo [3,2,0] heptan -3-yl)-acetate was obtained.

Yield: 44% m.p.: 64.1–64.9° C.

FAB-MS: 338 (MH$^+$), calcd for C$_{20}$H$_{19}$NO$_4$ 337

IR (KBr, cm$^{-1}$): 3000, 2880, 1750, 1719, 1646, 1444.

$^1$H NMR (CDCl$_3$), δ (ppm): 2.65–2.90 (3H, m), 3.20–3.30 (2H, m), 3.47 (0.4H, dd, J=11, 6.6), 4.04 (0.6H, dd, J=11, 6.3), 4.67 (1H, m), 5.15 (0.4H, d, J=2.5), 5.27 (0.6H, d, J=2.5), 6.90 (0.4H, s), 6.91 (0.6H, s),, 7.32 (10H, m).

EXAMPLE 19

Sodium 2-(7-oxo-4-oxa-1-azabicyclo [3,2,0] heptan-3-yl)-acetate (Ex. 19)

Diphenylmethyl 2-(7-oxo-4-oxa-1-azabicyclo [3,2,0] heptan-3-yl)-acetate (674 mg, 2 mmol) obtained in example 18 was hydrogenated with 600 mg of 10% palladium on activated carbon in 20 ml of ethyl acetate at 50 psi hydrogen pressure at room temperature for 2 hrs. after removal of catalyst by filtration, the desired product, sodium 2-(7-oxo-4-oxa-1-azabicyclo [3,2,0] heptan-3-yl)-acetate (360 mg) was obtained as white solid with precipitation by adding 1 ml of sodium 2-ethyl hexanoate (2M solution in ethanol).

Yield: 93% m.p.: 70° C. (dec.)

IR (KBr, cm$^{-1}$): 3420, 2965, 1770, 1732, 1628, 1577, 1394.

$^1$H NMR (CDCl$_3$), δ (ppm): 2.05–2.15 (1H, m), 2.30–2.80 (2.35H, m), 3.87 (0.65H, dd, J=11.6, 6), 3.15–3.35 (2H, m), 4.35–4.55 (1H, m), 5.07 (0.35H, d, J=2.5), 5.23 (0.65H, d, J=2.5).

EXAMPLE 20

N-{(7-oxo-4-oxa-1-azabicyclo [3,2,0] heptan-3-yl)-methylcarbonyl} L-proline benzyl ester (Ex. 20)

To solution of sodium 2-(7-oxo-4-oxa-1-azabicyclo [3,2,0] heptan-3-yl)-acetate (194 mg, 1 mmol) in 2 ml of DMSO and 10 ml of dichloromethane, ethyl chloroformate (109 mg, 1 mmol) was added at −15° C. After stirring at −15° C. for 30 mins, a precooled (ca. −10° C.) solution of L-proline benzyl ester hydrochloride (242 mg, 1 mmol), triethylamine (110 mg, 1.1 mmol) in chloroform (8 ml) was added at −10° C. The resulting mixture was stirred at −10 to 0° C. for 2 hrs and at room temperature overnight, and then diluted with chloroform, washed with water, dried over sodium sulfate. After removal of solvent, the residue was purified by silica gel column chromatography using hexane-ethyl acetate (1:2) as eluent and 80 mg of the title compound was obtained.

Yield: 22%

$^1$H NMR (CDCl$_3$), δ (ppm): 1.85–2.30 (4H, m), 2.45–2.90 (3.35H, m), 4.05–4.20 (0.65H, m), 3.20–3.70 (4H, m), 4.40–4.80(2H, m), 5.05–5.30 (3H, m), 7.34 (5H, m).

Testing of inhibitors for inhibition of cathepsin B, L and papain

TEST EXAMPLE 1

In vitro assay procedure for papain

To a 170 μl of enzyme-buffer mixture (enzyme: papain, diluted to give 30 mOD/min, buffer: 0.2 M potassium phosphate, 1.0 mM EDTA, 5 mM L-Cysteine, pH 6.5) a 10 μL of inhibitor (dissolved in DMSO) was added. After 10 min of incubation at room temperature, a 20 μl of 10 mM substrate (N-CBZ-Pro-Phe-Arg-pNA, dissolved in DMSO) was added to initiate reaction. Reading is followed up for 3 min at the Thermomax plate reader (absorbance at 405 nm)

A plot of percentage of inhibition vs inhibitor concentration is obtained, and IC50 is determined using a linear regression calculations (concentration of inhibitor which will give 50% inhibition).

TEST EXAMPLE 2

In vitro assay procedure for cathepsin B

The compounds of formula I were tested for inhibition of cathepsin B using the known method (A. J. Barret et al., Biochem. J. 1982, 201, 189–198). To a 170 μl of enzyme-buffer mixture (enzyme: rat cathepsin B, diluted to give approximate 10 F units/min, buffer: 56 mM sodium acetate, 1.124 mM EDTA, 10 mM DTT, pH 5.1), a 10 μL of inhibitor (dissolved in DMSO) was added. After 10 min of incubation at room temperature, a 20 μl of 5 mM substrate (N-CBZ-Phe-Arg-AMC, dissolved in DMSO) was added to initiate reaction. Reading is followed up for 10 min at the fluoroscan reader (excitation at 380 nm, emission at 460 nm).

A plot of percentage of inhibition vs inhibitor concentration is obtained, and IC50 is determined using a linear regression calculations (concentration of inhibitor which will give 50% inhibition).

TABLE 1

In vitro inhibitory activity of compound of formula I on cysteine proteases (I)

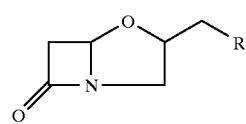

| Example No. | R | IC50 (μM) Papain | IC50 (μM) Cathepsin B |
|---|---|---|---|
| 1A | (3R,5S) tert-butyldimethylsilyloxy | 0.16 | 0.778 |
| 1B | (3R,5R) tert-butyldimethylsilyloxy | 3.10 | 7.78 |
| 2 | (3R,5S) hydroxy | 2.03 | 5.0 |

TABLE 1-continued

In vitro inhibitory activity of compound of formula I on cysteine proteases

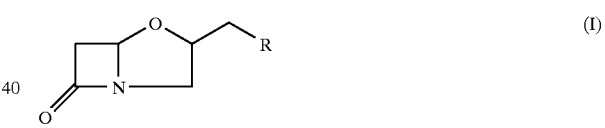
(I)

| Example No. | R | IC50 (μM) Papain | IC50 (μM) Cathepsin B |
|---|---|---|---|
| 3 | (3S,5S) acetylamino | 0.59 | 0.56 |
| 4 | (N—Cbz—L-phenylalanyl)oxy | 0.24 | 0.59 |
| 5 | (N—Cbz—L-propyl)oxy | 0.49 | 0.44 |
| 6 | (N—Cbz—L-isoleucyl)oxy | 0.38 | 0.51 |
| 7 | (N—Cbz—L-Phenylalanyl-glycyl)oxy | 3.51 | 3.11 |
| 8 | (N—Cbz—L-isoleucyl-L-prolyl)oxy | 0.74 | 4.5 |
| 9 | (N—Cbz—L-leucyl-L-prolyl)oxy | 2.05 | 2.9 |
| 10 | 1,2-dihydro-4-methyl-2-oxo-quinolin-3-yl-carbonyloxy | 0.14 | 3.05 |
| 11 | cyclohexanecarbonyloxy | 1.0 | 0.79 |
| 12 | cyclopentanecarbonyloxy | 1.13 | 0.66 |
| 13 | (trans-3-phenylpropenoyl)oxy | 0.45 | 4.06 |
| 14 | (10-methylisoalloxazin-7-yl)-carbonyloxy | 0.76 | 16.94 |
| 15 | (7-ethoxycarbonyl-10-methylisoalloxazin-3-yl) | 1.24 | 2.89 |
| 16 | (1,2-dihydro-4-methyl-2-oxo-quinolin-3-yl)-carbonylamino | 0.70 | 4.20 |
| 17 | (3R,5S) (1,2,3-triazol-1-yl) | 0.29 | 0.29 |
| 18 | COOCH($C_6H_5$)$_2$ | 2.08 | 2.97 |
| 19 | COONa | 1.69 | 3.98 |
| 20 | CO—L—Pro—COOCH$_2$C$_6$H$_5$ | 0.56 | 13.7 |
| 21 | NHCOCH(NH$_2$)CH$_2$COOH | >20 | 12.6 |
| 22 | OCOCH(NH$_2$)CH$_2$COOH | >20 | >20 |
| 23 | (N—Cbz—L-Phenylalayl)amino | 0.35 | 2.4 |
| 24 | OCOCH$_2$CH$_2$CH(NH$_2$)COOH | 2.92 | 12.0 |
| 25 | OCOCH(CH$_3$)NH$_2$HCl | 3.31 | >20 |
| 26 | NHCOCH(CH$_3$)NH$_2$HCl | 2.91 | >20 |
| 27 | NHCOCH$_2$Cl | 0.9 | 0.4 |
| 28 | NHCOCF$_3$ | 0.84 | 0.33 |
| 29 | S(O)CH$_2$COONa | 3.9 | 0.38 |
| 30 | NHCOCH(CH$_3$)$_2$ | 0.95 | 0.46 |
| 31 | NHCOCH$_2$NHCOCH$_3$ | 4.1 | 2.6 |
| 32 | NHCO(CH$_2$)$_4$CH$_3$ | 2.3 | 2.3 |
| 33 | NHS(O)$_2$CH$_3$ | 0.91 | 0.95 |
| 34 | S(O)CH$_2$CH$_2$NHCOCH$_3$ | 3.8 | 14.6 |
| 35 | S(O)$_2$CH$_2$COONa | 12.9 | 0.74 |
| 36 | OCO(CH$_2$)$_{14}$CH$_3$ | >50 | >50 |
| 37 | OCOCH=CHCOONa | 19 | 1.9 |
| 38 | NHCO(CH$_2$)$_5$OCHO | 2.2 | 3.5 |
| 39 | NH$_2$HCl | 5.5 | 5.5 |
| 40 | NHCOCH$_2$NHCOCH(NH$_2$)CH$_2$COOH | 8.3 | 15.9 |
| 41 | OH (3,5-trans, 5,6-trans) | 4.5 | 22.5 |
| 42 | OH (3,5-cis, 5,6-trans) | >100 | >100 |
| 43 | OCOCH(NHCOCH$_3$)(CH$_2$)$_4$NHCOCH$_3$ | 1.77 | >70 |
| 44 | OCOCH$_3$ | 0.21 | 1.10 |
| 45 | NHCOCHOH | 1.693 | 5.0 |
| 46 | anthaquinone-2-carbonyloxy | 0.021 | 0.53 |
| 47 | NHCOC$_6$H$_3$(3,4-OCH3) | 0.13 | 8.8 |
| 48 | SC$_6$H$_5$ | 0.85 | 0.42 |
| 49 | NHCOCH(NH$_2$HCl)CH$_2$C$_6$H$_5$ | 0.62 | 3.08 |
| 50 | OCOC$_6$H$_3$(3,4-OH) | 2.5 | 0.46 |
| 51 | OCOC$_6$H$_3$(3,4-OCH$_3$) | 0.13 | 3.3 |
| 52 | OCOC$_6$H$_2$(3-OCH$_3$, 4-OH, 5-OCH$_3$) | 0.62 | 3.1 |
| 53 | OCOC$_6$H$_4$(4-NH$_2$) | 2.4 | 3.8 |
| 54 | OCOC$_6$H$_2$(2,4,5-F) | 0.66 | 8.3 |
| 55 | OCOC$_6$H$_4$(4-CN) | 0.74 | 3.7 |
| 56 | NHS(O)$_2$C$_6$H$_4$(4-CH$_3$) | 1.76 | 0.67 |
| 57 | NHS(O)$_2$C$_6$H$_4$(4-Cl) | 0.63 | 0.63 |
| 58 | NHCOC$_6$H$_5$ | 0.81 | 4.1 |
| 59 | NHS(O)$_2$C$_6$H$_4$(4-OCH$_3$) | 3.2 | 0.64 |
| 60 | OCOC$_6$H$_5$ | 4.0 | 4.0 |
| 61 | S(O)$_2$C$_6$H$_5$ | 1.6 | 1.6 |
| 62 | S(O)CH$_2$C$_6$H$_5$ | 0.76 | 8.7 |
| 63 | OCOC$_6$H$_4$(4-OCH$_2$COONa) | 2.9 | 2.0 |
| 64 | OCOC$_6$H$_4$(2-COONa) | 16.0 | 6.9 |
| 65 | OCOC$_6$H$_4$(4-OCH3) | 2.0 | 8.9 |
| 66 | OCOC$_6$H$_4$(4-F) | 2.4 | 3.8 |
| 67 | OCOC$_6$H$_4$(4-OH) | 2.4 | 3.8 |
| 68 | NHCOC$_6$H$_4$(4-OCH$_3$) | 0.72 | 3.6 |
| 69 | OCOCH(CH$_2$OH)NHCOOCH$_2$C$_6$H$_5$ | 1.5 | 2.7 |
| 70 | OCOCH$_2$NHCOCH$_2$NHCOOCH$_2$C$_6$H$_5$ | 0.35 | 6.7 |
| 71 | OCOCH(OH)CH(C$_6$H$_5$)NHCOC$_6$H$_5$ | 0.24 | 0.24 |
| 72 | 1,2-triazol-1-yl | 0.66 | 0.68 |
| 73 | (2-oxo-azetidin-4-yl)oxy | 2.4 | 4.7 |
| 74 | 6-(1,2,3-triazol-1-yl)-hexanecarbonylamino | 3.3 | 6.5 |
| 75 | cyclohexanecarbonylamino | 3.97 | 0.36 |
| 76 | (2-carboxy-cyclohexan-1-yl)-carbonyloxy | 10.9 | 0.34 |

We claim:

1. A method of treating cancer metastasis sensitive to the compound of formula I without treating the cancer per se in a patient in need of such treatment, comprising administering to the patient a cancer metastasis treating effective amount of a compound of formula I,

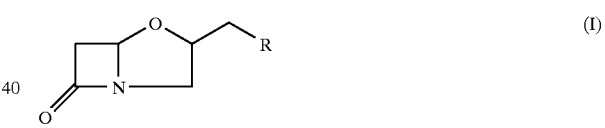
(I)

wherein

R is selected from the group consisting of OR$_1$, —OCOR$_1$, —COOR$_1$, CONHR$_1$ NHR$_1$, —NHCOR$_1$, —NHSO$_2$R$_1$, SOnR$_1$ and a mono, bi or tricyclic 5–14 membered heterocyclic ring having 1–4 heteroatoms independently selected from N, S and O, wherein n is 0,1 or 2, R$_1$ is selected from the group consisting of (a) hydrogen, (b) C1–C6 alkyl which is unsubstituted or substituted by 1–3 substituents independently selected from the group consisting of (1) OR$_2$, (2) halogen, (3) cyano, (4) NR$_3$R$_3$, (5) carboxy, (6) a mono, bi or tricyclic 5–14 membered heterocyclic ring having 1–4 heteroatoms independently selected from N, S and O and (7) phenyl, wherein the phenyl is unsubstituted or substituted by 1–2 substituents independently selected from the group consisting of OR$_2$, halogen, cyano, carboxy and NR$_3$R$_3$, (c) C2–C4 alkenyl which is unsubstituted or has a substituent selected from the group consisting of (1) hydroxy, (2) halogen, (3) carboxy, (4) a mono, bi or tricyclic 5–14 membered heterocyclic ring having 1–4 heteroatoms independently selected from N, S and O and (5) phenyl, wherein the phenyl is unsubstituted or substituted by 1–2 substituents independently selected from the group consisting of $OR_2$, halogen, cyano, amino and carboxy, (d) C2–C4 alkynyl, (e) C3–C6 cycloalkyl, (f) C5–C6 cycloalkenyl, (g) a phenyl group which is unsubstituted or substituted by 1–3 substituents independently selected from the group consisting of $OR_2$, halogen, carboxy, cyano, $NR_3R_3$, C1–C4 alkyl and C1–C2 alkoxy, (h) a mono, bi or tricyclic 5–14 membered heterocyclic ring having 1–4 heteroatoms independently selected from N, S and O and (i) 1–2 amino acids in which amino groups are unprotected or protected with $R_4$, or carboxylic groups are unprotected or protected with $R_7$, $R_2$ is selected from the group consisting of (a) hydrogen, (b) C1–C4 alkyl which is unsubstituted or substituted by 1–2 substituents independently selected from the group consisting of hydroxy, halogen, cyano, carboxy, amino and phenyl and (c) a phenyl group which is unsubstituted or substituted by 1–3 substituents independently selected from the group consisting of hydroxy, halogen, carboxy, cyano, amino, C1–C4 alkyl, and C1–C2 alkoxy, $R_3$ is selected from the group consisting of (a) hydrogen, (b) C1–C4 alkyl which is unsubstituted or substituted by 1–2 substituents independently selected from group consisting of hydroxy, halogen, cyano, carboxy and amino, (c) a phenyl group which is unsubstituted or substituted by 1–3 substituents independently selected from the group consisting of hydroxy, halogen, carboxy, cyano, amino, C1–C4 alkyl, and C1–C2 alkoxy and (d) $COR_5$ wherein $R_5$ is C1–C4 alkyl or phenyl, wherein the phenyl is unsubstituted or substituted by 1–3 substituents independently selected from the group consisting of hydroxy, halogen, carboxy, cyano, amino, C1–C4 alkyl, and C1–C2 alkoxy, $R_4$ is selected from the group consisting of (a) $COOR_6$, (b) $COR_6$ and (c) $SO_2R_6$, wherein $R_6$ is selected from the group consisting of (1) C1–C4 alkyl which is unsubstituted or substituted by 1–2 substituents independently selected from (i) hydroxy, (ii) halogen, (iii) cyano, (iv) carboxy, (v) amino, (vi) phenyl, wherein the phenyl is unsubstituted or substituted by 1–3 substituents independently selected from the group consisting of hydroxy, halogen, carboxy, cyano, amino, C1–C4 alkyl and C1–C2 alkoxy and (vii) a mono or bicyclic 5–10 membered heteroaryl ring having 1–3 heteroatoms independently selected from N, S and O and (2) a phenyl group which is unsubstituted or substituted by 1–3 substituents independently selected from the group consisting of hydroxy, halogen, carboxy, cyano, amino, C1–C4 alkyl, and C1–C2 alkoxy, and $R_7$ is selected from the group consisting of (a) C1–C4 alkyl group which is unsubstituted or substituted by 1–2 substituents independently selected from the group consisting of (i) hydroxy, (ii) halogen, (iii) cyano, (iv) carboxy, (v) amino, (vi) phenyl, wherein the phenyl is unsubstituted or substituted by 1–3 substituents independently selected from the group consisting of hydroxy, halogen, carboxy, cyano, amino, C1–C4 alkyl and C1–C2 alkoxy and (vii) a mono or bicyclic 5–10 membered heteroaryl ring having 1–3 heteroatoms independently selected from N, S and O and (b) a phenyl group which is unsubstituted or substituted by 1–3 substituents independently selected from the group consisting of hydroxy, halogen, carboxy, cyano, amino, C1–C4 alkyl and C1–C2 alkoxy, or a physiologically acceptable salt thereof or an optical isomer thereof.

2. The method of claim 1, wherein the compound is a diastereoisomer in which the hydrogen atoms at C3 and C5 are trans to each other.

3. The method of claim 1, wherein the physiologically acceptable salt is selected from the group consisting of sodium, potassium, magnesium, calcium, hydrogen chloride, tartaric acid, succinic acid, fumaric acid and p-toluenesulfonic acid.

4. The method of claim 1, wherein the compound is administered by oral administration at a daily treatment dose of about 50 to 1500 mg/day.

5. The method of claim 4, wherein the daily treatment dose is divided into 2 to 4 individual doses.

6. The method of claim 1, wherein the compound is administered by intravenous administration of an injection solution at a daily treatment dose of about 1 to 100 mg/day.

7. The method of claim 6, wherein the injection solution is diluted with a physiologically acceptable diluent and is administered over at least 5 minutes.

8. The method of claim 1, wherein the compound is administered by rectal administration at a daily treatment dose of about 1 to 1000 mg/day.

9. The method of claim 8, wherein the daily treatment dose is divided into two individual doses.

* * * * *

UNITED STATES PATENT AND TRADEMARK OFFICE
CERTIFICATE OF CORRECTION

PATENT NO. : 5,925,633
DATED : July 20, 1999
INVENTOR(S) : Singh et al

It is certified that error appears in the above-identified patent and that said Letters Patent is hereby corrected as shown below:

Column 2, Line 32, please delete " for treatment of diffrent diseases associated with cystein " and insert therefor, -- for treatment of diffrent diseases associated with cysteine --

Column 2, Line 57, please delete " R is selected from the group consisting of "$Or_1$." and insert therefor, -- R is selected from the group consisting of $OR_1$ --

Column 9, Line 49, please delete " $[\alpha]_D^{22} = -95°$ (c=2, CHC13): " and insert therefor, -- $[\alpha]_D^{22} = -95°$ (c=2, $CHCl_3$): --

Column 9, Line 57, please delete "$[\alpha]_D^{22} = +93°$ (c=2, CHC13):" and insert therefor, -- $[\alpha]_D^{22} = +93°$ (c=2, $CHCl_3$): --

UNITED STATES PATENT AND TRADEMARK OFFICE
CERTIFICATE OF CORRECTION

PATENT NO. : 5,925,633
DATED : July 20, 1999
INVENTOR(S) : Singh et al

It is certified that error appears in the above-identified patent and that said Letters Patent is hereby corrected as shown below:

Column 10, Line 9, please delete "$[\alpha]_D^{22}=-144°$ (c=2, CHC13);" and insert therefor, -- $[\alpha]_D^{22}=-144°$ (c=2, $^{CH}Cl_3$); --

Column 10, Line 58, please delete "$[\alpha]D^{23}$ (c=1.0, $CHCl_3$):-174°" and insert therefor, -- $[x]D^{23}$ (c=1.0, $CHCl_3$):-174° --

Signed and Sealed this

Nineteenth Day of December, 2000

Attest:

Q. TODD DICKINSON

*Attesting Officer*

*Commissioner of Patents and Trademarks*